United States Patent [19]

Guadalupi et al.

[11] 4,013,718
[45] Mar. 22, 1977

[54] INTEGRATED PROCESS FOR THE PRODUCTION OF UREA

[75] Inventors: Mario Guadalupi; Giorgia Pagani, both of Milan; Umberto Zardi, San Donato Milanese; Ivo Paris, Melegnano, all of Italy

[73] Assignee: Snam Progetti S.p.A., Milan, Italy

[22] Filed: Mar. 20, 1974

[21] Appl. No.: 453,028

Related U.S. Application Data

[63] Continuation of Ser. No. 177,629, Sept. 3, 1971, abandoned.

[30] Foreign Application Priority Data

Sept. 3, 1970 Italy .................... 29295/70

[52] U.S. Cl. ...................... 260/555 A; 423/359
[51] Int. Cl.² ........................... C07C 126/00
[58] Field of Search ............ 260/555 A, 555 R; 423/359

[56] References Cited

UNITED STATES PATENTS

| | | | |
|---|---|---|---|
| 3,281,464 | 10/1966 | Tsao | 260/555 A |
| 3,303,215 | 2/1967 | Otsuka et al. | 260/555 A |
| 3,349,126 | 10/1967 | Hsu et al. | 260/555 A |
| 3,371,115 | 2/1968 | Cook et al. | 260/555 A |
| 3,607,939 | 9/1971 | Kaasenbrood et al. | 260/555 A |
| 3,666,807 | 5/1972 | Yamagishi et al. | 260/555 A |
| 3,674,847 | 7/1972 | Kaasenbrood et al. | 260/555 A |
| 3,684,442 | 8/1972 | Konoki et al. | 260/555 A |

*Primary Examiner*—Oscar R. Vertiz
*Assistant Examiner*—Eugene T. Wheelock
*Attorney, Agent, or Firm*—Ralph M. Watson

[57] ABSTRACT

Urea is produced through an integrated, isobaric process in which raw ammonia synthesis gas, consisting essentially of $H_2$, $N_2$ and sufficient $CO_2$ to produce the urea and compressed to a pressure slightly above the urea synthesis pressure, is decarbonated in a vertical film heat exchanger where it is contacted with a thin aqueous film containing $NH_3$ with which the $CO_2$ reacts to produce a concentrated carbamate solution that is withdrawn from the bottom of the exchanger and fed to a urea reactor. The compressed, unreacted synthesis gas containing traces of CO and saturated with $NH_3$ is withdrawn from the upper part of the heat exchanger, $NH_3$ is separated therefrom and recycled to the heat exchanger, and the balance of the unreacted synthesis gas is subjected to methanation to eliminate any CO and $CO_2$ therein. The methanated gas and the gases from an ammonia synthesis reactor are fed to the lower part of a vertical film absorber where they meet, in counter-current, a film of water or a dilute solution of $NH_3$, fed to the top of the film absorber, which absorbs the $NH_3$ in the gases. A concentrated $NH_3$ solution, withdrawn from the film absorber as bottom product, is fed to the vertical film heat exchanger at vertically spaced points and heat is wit-drawn from that exchanger at a rate that is regulated to maintain the temperature in the heat exchanger above the carbamate crystallization temperature. Synthesis gas is withdrawn from the top of the film exchanger, cooled to condense a dilute $NH_3$ solution that is withdrawn, additionally cooled and dried through treatment with liquid ammonia in a Venturi tube, and then fed to an ammonia synthesis reactor. A solution of urea, carbamate and excess $NH_3$ flows from the urea reactor to a carbamate decomposer from the top of which carbamate decomposition products flow directly to the urea reactor, and an aqueous urea solution and equilibrium $NH_3$ are withdrawn from the bottom of the carbamate decomposer.

4 Claims, 1 Drawing Figure

INTEGRATED PROCESS FOR THE PRODUCTION OF UREA

Figure 1:
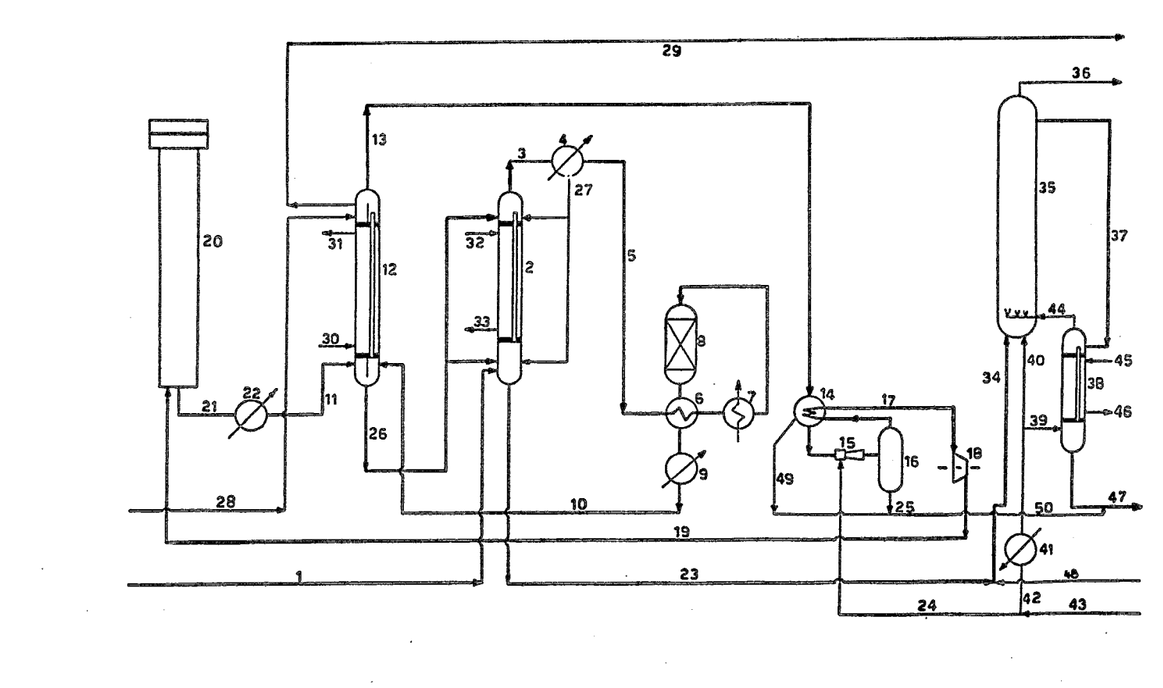

This is a continuation of application Ser. No. 177,629, filed Sept. 3, 1971, now abandoned.

The present invention relates to an integrated process for the production of urea.

More particularly this invention relates to a process for the production of a very concentrated aqueous solution of ammonium carbamate obtained through absorption of the $CO_2$, present in the raw gases of the in an ammonia synthesis, by the aqueous solution of ammonia coming from the same synthesis; and to the subsequent conversion into urea of the ammonium carbamate solution obtained in that way.

Usually the production of urea on an industrial scale is carried out in two plants, each independent of the other, namely: a plant for the production of liquid ammonia having carbon dioxide as a by-product, and another plant for the production of urea through the synthesis of the two cited products. In every case wherein the final product is mainly urea, ammonia may be considered as an intermediate, with the consequent possibility of integrating the two types of plant.

An ideal scheme of integration is the one wherein there is utilized the capacity of direct reaction between ammonia and carbon dioxide with formation of carbamate to be converted subsequently into urea, thus avoiding two expensive separation operations typical of the ammonia line, such as the removal of the carbon dioxide from converted gas by means of solvents, and further compression of the gaseous carbon dioxide produced through the regeneration of the solvent up to the urea synthesis pressure, and the separation, through liquefaction, of the ammonia from the unreacted gases coming from the synthesis reactor.

The advantages obtained through such a scheme are the following:

saving of thermal energy required by the conventional decarbonation plant;

saving of thermal or mechanical energy required in the separation of the ammonia from the unreacted gases;

saving on the plant cost by the elimination of the ammonia separation stage;

saving of the mechanical energy for the $CO_2$ compression;

saving on the plant cost for the $CO_2$ compression.

Subjecting the ammonia production to the production of urea may apparently be considered as a negative aspect of the integrated process.

We have said "apparently" since as a matter of fact the integrated scheme will be accepted only in those cases wherein all or at least a lot of the produced ammonia is converted into urea.

Then ammonia must be considered in these types of plants as an intermediate product.

Integrated processes for the production of urea are well known in the art; one of them invalves the compression of the raw gases for the ammonia synthesis and the forwarding of them to a column; the upper part of such column is employed for the absorption of $CO_2$ by means of ammonia solutions and subsequent formation of carbamate, the lower part is used for the conversion of the produced carbamate into urea.

The strong development of heat produced in the formation of the carbamate and the presence of inerts ($H_2 + N_2$) which reduce the partial pressure of the $NH_3$ and of the $CO_2$ makes it necessary to operate at high pressures (about 250 kg/cm$^2$) to maintain the reactants in the liquid phase; in the scheme of such a process there is no means for removing such heat as it develops and a balance is obtained by the introduction of cold absorbing solutions. The conversion of the carbamate into urea is effected in the same in apparatus, Namely in the lower part of it. As noted above, the difficulty in removing the heat and the presence of the inerts $H_2 + N_2$ makes it necessary in order to have sufficient partial pressure of the carbon dioxide, to operate at rather high pressures.

The absorbing solution is formed of anhydrous ammonia to which an aqueous solution of the decomposition products of the unconverted carbamate is added. Such decomposition is carried out at low pressure.

The raw gases for the synthesis after the absorption of the $CO_2$ and after other treatments are forwarded to the the ammonia synthesis reactor at high pressure, namely between 400 and 500 kg/cm$^2$.

From the fact that the ammonia produced and employed to obtain the aqueous absorbing solution is anhydrous at the beginning may be deduced the fact that its separation from the effluents of the synthesis occurs through suitable means, namely through water refrigeration and through vaporizing ammonia, also because of its high synthesis pressure.

In another integrated process not all the raw gases constituting the synthesis feed are the absorption of the $CO_2$ therein contained, but part is conventionally treated to obtain pure $CO_2$. This has been done because the carbamate formation and its transformation into urea are carried out in two different apparatuses, then, to maintain the temperature of the zone wherein urea forms at acceptable values, ammonia and carbon dioxide are sent thereto, and they supply the necessary heat by reacting into carbamate.

The absorption of the $CO_2$ from the raw synthesis gases for the production of carbamate is effected at pressures lower than the pressure of the urea synthesis; aqueous solutions containing the products of decomposition of the carbamate not transformed into urea and occasional additions of ammonia being utilized.

Then the carbamate decomposition products are scrubbed, partially in the column to which the raw synthesis gases are sent for absorbtion of $CO_2$, and partially in a second column, whereto a diluted ammonia solution is sent as absorber. The solution coming out from this second column is sent as absorbing means to the aforesaid first column.

The raw synthesis gases, after the removal of the $CO_2$ and the subsequent known treatments, go to the ammonia synthesis.

We have discovered, which is the subject of the present invention, an integrated process for the production of urea which makes it possible to obtain the advantages indicated above in a completely original way together with other advantages which are particular characteristics of this process.

Basic characteristics of the process according to the present invention are:

the use of particular types of apparatuses in the cases wherein besides the material exchange the heat exchange is also very important without excluding obviously the use of any apparatus suitable to this purpose;

a particular method for the dehydration of the gases to be sent to the ammonia synthesis which is already known from the Italian Pat. No. 891,098, and its addition, Italian Pat. No. 29055 A/70, filed on Aug. 27, 1970 owned by the assignee of this application;

the separation of the ammonia from the effluents of the ammonia synthesis reactor through water absorption and the direct use of ammonia solution obtained in this way to remove $CO_2$ from the converted gas thus producing carbamate;

sending said solution, containing all the $CO_2$ of the feed directly to the urea reactor;

an original isobaric cycle of transformation of the carbamate into urea including also the stage of decomposition of the intransformed carbamate into urea, which stage of decomposition is known partially from the Italian Pat. Nos. 694,929 and 812,030 owned by the assignee of this application.

The advantages derived from the particular practices followed in the process according to the present invention, besides other characteristics of our invention, will be made clearer hereinafter.

In any event, it will be appreciated from the following description that the process of this invention permits a remarkable reduction of the investment costs, since it requires, other factors being equal, a lower number of apparatuses and it also permits lower operating costs as it reduces remarkably the consumption of mechanical energy and the consumption of thermal energy per ton of urea produced.

Further objects and advantages of the present invention will be made clear by the specification and examples which will be reported hereinafter. In the integrated process for the production of urea, which is subject for this invention, the raw gases of the ammonia synthesis, coming from a steam are forming or produced in any other conventional way, and wherein the carbon monoxide has been almost completely converted, are compressed to a pressure slightly higher than that of the urea synthesis; after the compression said gaseous/stream, still containing all the carbon dioxide necessary for the production of urea, is sent to the bottom of a vertical tubes exchanger, wherein it meets in countercurrent inside the tubes a film of ammonia solution, and is produced; the heat of reaction is removed by causing a cooling fluid, for instance water for feeding the boilers, to flow from the jacket side of the film exchanger. The selection of this type of apparatus is obviously not limitative, other suitable types of apparatus being usefully employable. The carbamate which has been formed comes out from the bottom of said exchanger, wherein the temperature range is between 100° and 250°C and the pressure range is between 100 and 250 kg/cm², as a very concentrated solution which is sent for transformation into urea. Such a transformation will be described hereinafter. The absorbing solution may be sent to the top of the exchanger and also to the bottom. The gaseous decarbonized stream containing the ammonia of saturation, goes out from the top of the exchanger and passes into a cooler where a part of the ammonia of saturation condenses and is forwarded again to the exchanger, preferably to the bottom of the same.

The cooled gas is sent to methanation, after being suitably preheated, in suitable exchangers; at the outlet of the methanation stage the gas is caused to flow, after the recovery of the heat obtained through the cooling, to another vertical tubes exchanger wherein, in counterflow, it meets a water film or dilute ammonia solution, which absorbs the ammonia contained in the gases; said film exchanger is also cooled by a cooling fluid, which flows along the side of the jacket, in such a way as to have in the exchanger a temperature ranging from 10° to 60°C; the pressure ranges from 100 to 250 kg/cm². Also in this case the selection of this type of apparatus is not limitative in the sense that any other type of suitable apparatus may usefully be employed. The gases coming from the ammonia synthesis arrive at said exchanger and they also meet, in counterflow, water or a dilute ammonia solution which absorbs practically all the ammonia present in the gases.

From the bottom of this second exchanger comes a very concentrated ammonia solution (for instance 75 – 85% b.w.) which is sent as absorbing means to the first film exchanger where it absorbs the $CO_2$, producing carbamate.

In the top of the second exchanger there is a venting of a part of the gaseous stream coming from the ammonia synthesis to avoid the accumulation of inerts.

The gaseous mixture obtained in this way saturated with water is subsequently sent to dehydration which is effected through a "quench" with ammonia as described in said Italian Pat. No. 891,098 and in its Italian Pat. of addition application No. 29055 A/70 filed on Aug. 27, 1970.

In short, the gases are dehydrated by sending liquid ammonia, which mixes thoroughly with such gases and partially evaporates, in an apparatus adapted to provide a large surface of exchange between gas and ammonia.

Both the condensation due to the cooling caused by the adiabatic evaporation of a part of the ammonia and the dissolving of the ammonia itself, made easy by the large area of exchange between gas and ammonia, causes the removal of the last traces of the water from the gases, such removal having been already effected in a good portion in a heat exchanger, wherein a lot of the refrigeration units of the dehydrated gas are recovered said gas being made to flow in countercurrent to the gas still to be treated.

Immediately downstream of the above ammonia gas contacting, which may be carried out, for instance in a Venturi tube, a gas-liquid separator is present wherefrom the cooled gases are sent to the above-mentioned heat exchanger and a very concentrated ammonia solution, which is preferably added to the urea solution issued from the carbamate decomposer downstream of the urea reactor as shall be explained hereinafter.

To such a separated solution is preferably added also the weak ammonia solution which is formed in the heat exchanger wherein the dehydrated gas refrigeration units are recovered.

The gases treated in such a way are compressed to the ammonia synthesis pressure, between 100 and 250 kg/cm², then sent to the corresponding reactor.

The gases issued from the above reactor have been cooled then sent to the ammonia absorption and to the subsequent treatments as described above.

The fresh carbamate solution, together with the recycling carbamate and ammonia, was sent to the bottom of the urea reactor in the same zone wherein the vapors issued from the carbamate decomposer are injected; said vapors condense and furnish the necessary heat for the thermal balance of the reactor. The temperature, which may be adjusted by the amount of the vapors introduced into the reactor, may vary from 150° to 250 C; the pressure from 100 to 250 atmospheres. The urea, carbamate and urea solution, issued from the top of the reactor, is sent by gravity or by any other suitable means to the carbamate decomposer wherein is heated by means of the condensing vapor; it is also possible to employ vaporized $NH_3$ which flows in countercurrent and plays the roles of stripping means, in which conditions some of the carbamate and most of the dissolved ammonia are stripped and sent back to the reactor. The urea solution obtained in such a way expands and goes, with the inerts vented out of the reactor, to subsequent treatments known in the art.

However, it is to be noted that the process according to the present invention does not exclude the possibility of carrying out the ammonia synthesis at higher pressures also if such a pressure range is preferable. It is to be noted further that, if deemed suitable, between the above two film exchangers, an operation of fractional distillation may be interposed, in the sense that the concentrated ammonia solution produced in the first of two exchangers, before being sent as absorbing solution to the exchanger wherein the carbamate is formed, may be subjected to fractional distillation, according to the known art, in order to obtain liquid ammonia and water or very dilute ammonia solution. The liquid ammonia is then preferably sent to the bottom of said second film exchanger and the water or the dilute ammonia solution is sent to its top in order to allow it to flow in countercurrent inside the tubes as film to encounter the gas to be decarbonated.

It is also evident that it is possible to use only part of the process according to the present invention, when instead of the gases issued from the ammonia synthesis a $CO_2$ rich gas is available. In fact, apart from the ammonia synthesis and the gas treatments used for the above synthesis, by using any ammonia solution, it is possible to employ the carbamate formation stage, the carbamate dehydration to urea stage and the undehydrated carbamate decomposition stage according to the present invention where the production of urea is sought.

It is also to be noted that in the process according to the present invention it is possible to work at a substantially lower pressure in the ammonia synthesis. In most cases of the ammonia synthesis at low pressure, the separation of the ammonia itself from the synthesis effluents has been carried out by condensing the ammonia in the heat exchangers cooled by evaporating ammonia. The effective dehydration system of the recycle gas according to the present invention allows the removal of the ammonia from the synthesis effluent gases in a much cheaper and more efficient way, by making it possible to use apparatus which presents, at the same time and over a single surface, a very good heat and material exchange. This allows among other things, the double use of the water introduced into the cycle, first to absorb ammonia then to form the concentrated carbamate solution to be sent to transformation to urea.

Another very important aspect of the process according to the present invention is that it permits the main apparatus of the process such as the ammonia synthesis reactor, the absorber of the ammonia coming out from this reactor, the $CO_2$ absorber wherein the carbamate is formed, the carbamate-urea conversion reactor and the decomposer of the carbamate which is not transformed into urea, to work at substantially the same pressure, between 100 and 150 atmospheres, with all the favorable consequences derived therefrom. The possibility of working at different pressures in the different stages is not be be excluded. In such a case the pressure range may be fixed between 30 and 300 atm. Furthermore the operating procedure, in so far as the urea solution is concerned, in the process according to the present invention, and the injection of the vapors produced in the carbamate decomposer directly in the bottom of the urea reactor, besides resolving the thermal problems of such a reactor, permit elimination of the relative condenser, which is always a critical point in the urea plants because of the important corrosion problems occurring in such an apparatus. As already said, the absorption operation of the $NH_3$ out of the ammonia synthesis gases and the removal of the $CO_2$ from the raw gases of the ammonia synthesis with formation of carbamate can take place in any kind of suitable apparatus; however it is preferable that the difficult operation of the carbamate production takes place in a film exchanger, i.e. an apparatus which permits an effective heat and material exchange on a single surface; which is also valid for the ammonia absorption.

The heat of formation of carbamate is mostly recovered as, for instance, by preheating water to be fed to the boilers which circulates outside the pipes concurrent with the liquid film in order to maintain it at a temperature higher than that of the carbamate crystallization.

The drying of the wet synthesis gases is carried out by using a part of the ammonia to be recycled to the urea section, hence saving the energy required for the ammonia separation and eliminating in this way the relative injection pump.

The urea cycle has been designed so as to annul negative facts like the lack of the heat of formation the carbamate in of the reactor and the injection of a larger amount of water into the cycle.

In fact, due to the lack of the heat of formation of carbamate, the thermal level of the reactor has to be maintained by an external heat source. The more convenient way to furnish such heat is to use the heat content of the vapors issued from the carbamate decomposer by injecting them directly into the reactor; in such a way both the reagents preheating stage and the carbamate condensation stage are eliminated, by simplifying to a considerable extent the urea synthesis loop which is restricted only to the reactor and to carbamate decomposer. The thermal level of the urea reacted may be varied, if desired, by varying the amount of the carbamate decomposition vapors recycled to the reactor itself. Moreover the injection into the urea cycle of the process water necessary for producing the ammonia solution, and subsequently, the fresh carbamate solution, involves the $NH_3/CO_2$ ratio and the temperature being equal, a reduction of the reactor yield.

However, this does not occur when, according to the process of the present invention, the larger amount of the water present in the reactor is used for suitably increasing the ammonia excess without substantially increasing the system pressure.

In a cycle, preferably isobaric like the one of the present process, it is in fact possible to realize large ammonia circulations in a closed circuit between decomposer and reactor, with a low amount of heat to be supplied, the conditions of the ammonia solution being very close to the critical conditions. Such conditions make it possible to realize in the reactor high $NH_3/CO_2$ ratios, in the range 2:1 to 12:1 (preferably 4:1 to 8:1), and consequently very high yields, and to reduce the supply of high level heat. It is evident, from the foregoing, that the integrated ammonia-urea process, which is the subject of the present invention, make it possible to obtain practically all the advantages which the integration of two processes may give, which advantages involve a substantial reduction of the urea production cost.

There is now given by way of example a possible embodiment of the process according to the present invention referring to the more general case wherein the treated gases are the raw gas coming from the ammonia synthesis.

With reference to the accompanying drawing, the raw synthesis gas, still containing all the carbon dioxide necessary for the urea production, is compressed to a pressure slightly higher than that of the urea synthesis, then injected, through 1, to the bottom of the vertical film heat exchanger 2 wherein it is "decarbonated" through the reaction of substantially all of the $CO_2$ contained therein with ammonia. This apparatus is substantially a film exchanger wherein the transformed gas flowing inside the tubes comes into contact with a film of ammonia solution thereby forming carbamate; the heat of reaction is removed for instance by circulating the boiler feed water outside the tubes; such water enters through 32 and comes out from 33. A very concentrated carbamate solution is produced which, through 23, is injected into the urea reactor.

The decarbonated gas, containing traces of $CO_2$ and saturation ammonia (by coming into contact with ammonia solution the gas tends to become saturated with ammonia) is sent, through 3 to the refrigerator 4, wherein from one side part of the ammonia condenses and is sent back through 27 to the vertical film heat exchanger 2. The cooled gas is then sent to methanation to eliminate by transformation into methane, according to known technique, the CO and the $CO_2$ therein present which are poisons for the ammonia synthesis catalyst: through 5 it is sent to the preheater 6, wherein it is heated with the methanated gas and, after a further preheating in the heat exchanger 7, it enters the reactor 8 wherein the methanation reaction takes place. The methanated gas, after the heat recovery in 6, is cooled in 9 and is sent, together with the gas coming out from the synthesis reactor 20 and cooled in 22, into the film absorber 12, wherein the ammonia present in the gas is absorbed by water or a diluted ammonia solution film moving downwardly inside the tubes and injected in 12 through 28. The heat of reaction is removed with cooling water flowing into the pipes, which enters through 30 and comes out from 31. The ammonia free gas is sent through 13 to the cold recovery apparatus 14, wherein the condensation of a diluted ammonia solution takes place which is sent, through 49 and 50 into the duct 47. The gas is additionally cooled and dried in the Venturi 15 by means of liquid ammonia injection through 24. All the water present is removed by ammonia and discharged, the form of a concentrated ammonia solution, through 25 from the separator 16. Such a concentrated ammonia solution is sent to the duct 47 through 50. The dried gas, after cold recovery in 14, is sent, through 17 to the circulating compressors 18 and therefrom, through 19, to the synthesis reactor 20. The vent gases are then removed from the top of film absorber 12 through 29.

The carbamate concentrate solution coming from 2, is mixed with a recycled carbonate solution, through 48, and through 34, the mixture is sent to the bottom of the reactor 35.

At the bottom of the reactor is also sent ammonia recycled from other plant sections through 43. Said ammonia flow is divided into two streams; one is sent to the dehydrating quench in 15, through 24, the other is vaporized in the exchanger 41, whereto arrives through 42, then partially sent part to the carbamate decomposer 38, through 39, wherein is provided in 38 $NH_3$ employed as stripping means and partially to the bottom of the reactor 35, through 40.

From the top of the reactor, through 36, the inerts are purged and from 37 a solution of urea, water and carbamate with a large excess of ammonia comes out and goes to the decomposer 38, wherein flows inside tubes encountering as a countercurrent vaporized ammonia entering the bottom of 38 through 39. From the mantel side a suitable heating means is injected which goes in through 45 and comes out from 46; in such a way, both due to the stripping effect of the vaporized ammonia and due to the heat given to solution coming out from the reactor, the decomposition of most of the carbamate present takes place and its removal as gaseous phase, as $NH_3$ and $CO_2$, together with big amounts of ammonia vapor. Through 44 the decomposition products of carbamate carried by the ammonia stream are injected in the bottom of the reactor 35; the aqueous urea solution, containing the equilibrium ammonia dissolved therein and practically carbamate free, is removed through 47 and goes to the subsequent treatments. In case, as aforesaid, it is not necessary to inject vaporized ammonia as stripping means to the decomposer 38, the duct 39 shall be eliminated.

In order to illustrate the advantages of the present invention without, however, establising any limitation thereof, a numerical example has been given with reference to the accompanying drawing.

EXAMPLE

The operating data are for a plant having a capacity corresponding to 1000 t/d of ammonia, 990 t/d thereof are transformed into ammonium carbamate to be converted into 1700 t/d of urea, and 10 t/d available for other uses. Into the vertical film heat exchanger 2 are introduced:

through 1, raw synthesis gas having the following characteristics:

| | | |
|---|---|---|
| flow | 151,900 | $Nm^3/h$ |
| pressure | 200 | $kg/cm^2$ abs. |
| temperature | 125 | °C |
| Composition: | | |
| $H_2$ | 61.22 % | Vol. |
| CO | 0.38 | " |
| $CO_2$ | 17.71 | " |
| $N_2$ | 19.95 | " |
| $CH_4$ | 0.50 | " |
| A | 0.24 | " | through 26, ammonia solution having the following characteristics:

| | | |
|---|---|---|
| flow | 78350 | kg/h |
| Composition | | |
| $NH_3$ | 78.8% | by weight |
| $H_2O$ | 21.2% | " |
| Temperature | 45 | °C | through 27 liquid ammonia having the following characteristics:

| | | |
|---|---|---|
| flow | 8500 | kg/h |
| temperature | 40 | °C |

From the same vertical film heat exchanger 2 come out:
through 23, carbamate and ammonia solution having the following characteristics:

-continued

| | | |
|---|---|---|
| temperature | 150 | °C |
| flow | 117050 | kg/h |
| Composition | | |
| NH$_2$COO NH$_4$ | 80.00 % | by weight |
| NH$_3$ | 5.90 % | " |
| H$_2$O | 14.10 % | " | through 3, decarbonated gas having the following characteristics:

| | | |
|---|---|---|
| flow | 154.900 | Nm$^3$/h |
| temperature | 75 | °C |
| pressure | 199.9 | kg/cm$^2$ abs. |
| Composition | | |
| H$_2$ | 60.02 % | by volume |
| CO | 0.38 % | " |
| N$_2$ | 19.58 % | " |
| CH$_4$ | 0.49 % | " |
| A | 0.23 % | " |
| NH$_3$ | 19.30 % | " |

The heat of reaction, consisting of 14,500,000 kcal/h, was recovered by preheating the boiler feed water up to 140° C. Into the film absorber 12 are introduced:

through 11, gases coming out from the synthesis reactor and having the following characteristics:

| | | |
|---|---|---|
| flow | 466,000 | Nm$^3$/h |
| pressure | 198 | kg/cm$^2$ abs. |
| temperature | 40 | C |
| Composition | | |
| H$_2$ | 56.12 % | by vol. |
| N$_2$ | 18.71 % | " |
| CH$_4$ | 8.77 % | " |
| A | 2.40 % | " |
| NH$_3$ | 14.00 % | " | through 10, methanated gas having the following characteristics:

| | | |
|---|---|---|
| flow | 141,960 | Nm$^3$/h |
| pressure | 198 | ata |
| temperature | 40 | °C |
| Composition | | |
| H$_2$ | 64.26 % | vol. |
| N$_2$ | 21.37 % | " |
| CH$_4$ | 0.94 % | " |
| A | 0.25 % | " |
| NH$_3$ | 13.18 % | " | through 28, water having the following characteristics:

| | | |
|---|---|---|
| flow | 16290 | kg/h |
| temperature | 40 | °C |

From the same film absorber 12 go out
through 13, synthesis gas having the following characteristics:

| | | |
|---|---|---|
| flow | 513600 | Nm$^3$/h |
| pressure | 197.8 | ata |
| temperature | 45 | °C |
| Composition | | |
| H$_2$ | 67.01 % | by volume |
| N$_2$ | 22.34 % | " |
| CH$_4$ | 7.97 % | " |
| A | 2.18 % | " |
| NH$_3$ | 0.50 % | " |
| water | 200 | kg/h | through 29, venting gas having the following characteristics:

| | | |
|---|---|---|
| flow | 521000 | Nm$^3$/h |
| pressure | 195 | kg/cm$^2$ absolute |
| temperature | −17 | °C |
| Composition: | | |
| H$_2$ | 66.00 % | % b.w. |
| N$_2$ | 22.00 % | " |
| CH$_4$ | 7.85 % | " |
| A | 2.15 % | " |
| NH$_3$ | 2.00 % | " |
| H$_2$O | 3 | ppm |

This gas, after the recovering of the refrigeration units in 14, is compressed by the compressor 18 up to 207 kg/cm$^2$ absolute and forwarded to the synthesis 20.

To the carbamate dehydration reaction 35, running at the pressure of 195 kg/cm$^2$ and capable to obtain a 70% conversion, are sent:

through 23, the afore cited carbamate and ammonia solution through 48, the recycle carbonate solution having the following characteristics:

| | | |
|---|---|---|
| flow | 39950 | kg/h |
| temperature | 100 | °C |
| Composition: | | |
| CO$_2$ | 30.9 | % b.w. |
| NH$_3$ | 39.0 | % " |
| H$_2$O | 30.1 | % " | through 40, ammonia having the following characteristics:

| | | |
|---|---|---|
| flow | 34780 | kg/h |
| temperature | 140 | °C | through 44, vapors coming out from the decomposer 38 having the following characteristics:

| | | |
|---|---|---|
| flow | 117370 | kg/h |
| temperature | 190 | °C |
| Composition: | | |
| CO$_2$ | 7.9 | % b.w. |
| NH$_3$ | 85.3 | % " |
| H$_2$O | 6.8 | % " |

From the same reactor comes out, through 37, the urea solution having the following characteristics:

| | | |
|---|---|---|
| flow | 309545 | kg/h |
| temperature | 180 | °C |
| Composition: | | |
| CO$_2$ | 7.2 | % b.w. |
| NH$_3$ | 51.3 | % b.w. |
| H$_2$O | 18.5 | % b.w. |
| Urea | 23.0 | % b.w. |

From the decomposer 38 goes out at the end, through 47, the urea solution which must be sent to the final treatment, having the following characteristics:

| | | |
|---|---|---|
| flow | 192175 | kg/h |
| temperature | 220 | °C |
| Composition: | | |
| CO$_2$ | 6.8 | % b.w. |
| NH$_3$ | 30.5 | % " |
| H$_2$O | 25.7 | % " |
| Urea | 37.0 | % " |

The heat requirement of the decomposer 38, is satisfied by sending, through 45, 55000 kg/h of steam of 40 kg/cm$^2$.

In the present example the sending of vaporized NH$_3$ to the decomposer 38 through 39 was not provided.

What we claim is:

1. Integrated process, for the production of urea which comprises compressing, the raw urea synthesis gases coming from steam reforming, or obtained in any other conventional manner, and consisting essentially of hydrogen, nitrogen and sufficient carbon dioxide to produce urea, to a pressure slightly higher than the urea synthesis pressure and, after compression, passing said raw urea synthesis gases still containing the carbon dioxide necessary for the production of urea to the bottom of a jacketted vertical film heat exchanger wherein it is counter-currently contacted with a film of ammonia solution to produce carbamate; removing reaction heat by causing a cooling fluid film to flow through said jacket; withdrawing the obtained carbamate from the bottom of said vertical film heat exchanger wherein the temperature rages between 100° and 250° C, as a very concentrated solution; withdrawing raw synthesis gases containing ammonia and free of carbon dioxide from the top of said vertical film heat exchanger and passing them into a cooler where a portion of the ammonia condenses, feeding said condensed ammonia to said vertical film heat exchanger, the cooled gas being methanated and after cooling the methanated gases are passed to a jacketted film absorber with vertical tubes wherein they meet in countercurrent flow a film of water or a very diluted aqueous solution of ammonia, which absorbs the ammonia contained in said methanated gases; cooling said film absorber by a cooling fluid which flows along the jacket side so as to maintain in said film absorber a temperature in the range 10°–60° C, its pressure being comprised between 100 and 250 kg/cm², said film absorber being provided at the bottom also with the gas coming from an apparatus for the synthesis of ammonia, from the bottom of said film absorber a concentrated ammonia solution is withdrawn and sent to said vertical film heat exchanger where it absorbs the $CO_2$, forming carbamate; from the top of the said film absorber venting part of the gaseous stream coming from the synthesis of the ammonia to avoid the accumulation of inerts, thereafter mixing said gaseous stream from the synthesis of ammonia and the methanated gases after having gone through said film absorber; the gaseous mixture so obtained, saturated with water being subsequently dehydrated by contact with liquid ammonia which is mixed thoroughly with said gaseous mixture in an apparatus that forms a large exchange surface between said gaseous mixture gas and ammonia, immediately downstream of such contact between ammonia and said gaseous mixture separating said gaseous mixture and said liquid ammonia; forwarding the separated gaseous mixture to said apparatus for the synthesis of ammonia after said gaseous mixture is compressed up to the synthesis pressure of ammonia, namely 100–250 kg/cm² and passing a solution of ammonia, to the urea solution coming from a carbamate decomposer combining the solution of the carbamate with ammonia which is forwarded to the bottom of a urea reactor in the same zone wherein are introduced the vapors coming from a carbamate decomposer, the temperature being regulated by the amount of the vapors introduced into the exchanger from said carbamate decomposer and ranges between 150° and 250° C., while the pressure ranges between 100 and 250 kg/cm²; withdrawing solution of urea, carbamate, ammonia and water from the top of the reactor which is sent to said carbamate decomposer where it is heated and stripped by means of $NH_3$ which flows countercurrently and acts as a stripping agent; the urea from the solution so obtained being thereafter separated.

2. An integrated, substantially isobaric process for the production of urea which comprises compressing a synthesis gas consisting essentially of hydrogen, nitrogen and sufficient carbon dioxide to produce the urea to a pressure slightly above the pressure in a urea reactor; passing said compressed synthesis gas to the bottom of a jacketted vertical film heat exchanger where it is counter-currently contacted with a liquid aqueous film containing ammonia so that a concentrated solution of carbamate is formed and substantially all of said carbon dioxide is removed from said synthesis gas; removing heat from the heat exchanger by circulating a coolant fluid through the jacket for said exchanger in a direction which is co-current with said liquid film so that the temperature in the exchanger is maintained above the crystallization temperature of the carbamate; withdrawing from the top of said vertical film heat exchanger the unreacted compressed synthesis gas, saturated with ammonia, and traces of carbon dioxide; separating a part of the ammonia from said unreacted synthesis gas and recycling said separated ammonia through the vertical film heat exchanger by feeding a portion thereof at the lower end and the balance at the upper end of said exchanger; subjecting the balance of said unreacted compressed synthesis gas to preheating and methanation and passing said methanated gas to a film absorber together with ammonia from an ammonia synthesis reactor and countercurrently contacting methanated gas and the ammonia from the ammonia synthesis reactor with water or a dilute aqueous solution of ammonia; withdrawing a liquid containing ammonia from the bottom of said film absorber and feeding said liquid to said vertical film heat exchanger at spaced points respectively adjacent its upper and lower ends; withdrawing the methanated gas from the top of the film exchanger and cooling said methanated gas to remove ammonia therefrom and then dehydrating said methanated gas by admixing it with liquid ammonia, then separating said ammonia therefrom and thereafter passing said dehydrated methanated gas to said ammonia synthesis reactor; withdrawing from the bottom of said vertical film heat exchanger said concentrated carbamate solution and passing it to the bottom of a urea reactor which is supplied with an ammonia feed and also feeding to said urea reactor directly from a carbamate decomposer the gaseous products of the decomposition of carbamate at a rate such that said urea reactor is maintained at a selected temperature; passing from the top of said urea reactor to said carbamate decomposer a mixture of water, urea, ammonia and carbamate, and feeding to said decomposer vaporized ammonia counter-currently to said mixture; withdrawing from the bottom of said carbamate decomposer an aqueous solution of urea together with equilibrium ammonia; and operating said ammonia synthesis reactor, film absorber, vertical film heat exchanger, urea reactor and carbamate decomposer at substantially the same pressure in the range of from 100 to 250 kg/cm².

3. Integrated process for the production of urea, according to claim 2 wherein the unreacted compressed synthesis gas coming out from the top of the vertical film heat exchanger, wherein carbamate forms, is made to pass into a cooler, wherein a part of the ammonia therein contained is condensed and is then recycled to the bottom of said vertical film heat exchanger.

4. Integrated process for the production of urea according to 2, wherein the ammonia solution produced in the film absorber, wherein is absorbed the ammonia contained in the effluents of the ammonia synthesis, before being sent as absorbing means to the vertical film heat exchanger, wherein there is the formation of carbamate, is subjected, according to conventional techniques, to topping so as to obtain liquid ammonia and water or diluted ammonia solution and then sending as absorbing means, to the top of said vertical film heat exchanger the water or the diluted ammonia solution while to the bottom is sent the ammonia.

* * * * *

UNITED STATES PATENT AND TRADEMARK OFFICE
CERTIFICATE OF CORRECTION

PATENT NO. : 4,013,718              Page 1 of 3
DATED : March 22, 1977
INVENTOR(S) : Mario Guadalupi, Giorgio Pagani, Umberto Zardi and Ivo Paris It is certified that error appears in the above-identified patent and that said Letters Patent are hereby corrected as shown below:

Column 1, line 60, Correct "invalves" to read --involves--.

Column 2, line 8, Before "apparatus" delete --in--.

line 8, Correct "Namely" to read --namely--.

line 11, After "necessary" insert a comma --,--.

line 18, Before "synthesis" insert --ammonia--.

line 31, After "are" insert --treated for--.

line 66, After "important" insert a comma --,--.

Column 3, line 4, After "Pat." insert --application--.

line 5, Before "owned" insert a comma --,--.

line 11, After "gas" insert a comma --,--.

line 16, Correct "intransformed" to read --untransformed".

UNITED STATES PATENT AND TRADEMARK OFFICE
CERTIFICATE OF CORRECTION

PATENT NO. : 4,013,718
DATED : March 22, 1977
INVENTOR(S) : Mario Guadalupi, Giorgio Pagani, Umberto Zardi and Ivo Paris It is certified that error appears in the above-identified patent and that said Letters Patent are hereby corrected as shown below:

Column 3, line 36, Before "subject" insert --the--.

line 37, Correct "are forming" to read --reforming--.

Column 5, line 2, Correct "250C" to read --250°C--.

line 53, Correct "efficient" to read --effective--.

Column 6, line 37, Before "the"(first occurrence) delete "of".

Column 7, line 5, Correct "make" to read -- makes--.

UNITED STATES PATENT AND TRADEMARK OFFICE
CERTIFICATE OF CORRECTION

PATENT NO. : 4,013,718
DATED : March 22, 1977
INVENTOR(S) : Mario Guadalupi, Giorgio Pagani, Umberto Zardi and Ivo Paris It is certified that error appears in the above-identified patent and that said Letters Patent are hereby corrected as shown below:

Column 8, line 37, Correct spelling of "establishing".

Column 9, line 26, Correct the line to read --temperature 40 °C--.

Column 10, line 33, Correct "of"(second occurence) to read --at-- line 53, Correct "rages" to read --ranges--.

Signed and Sealed this

Twenty-fourth Day of January 1978

[SEAL]

Attest:

RUTH C. MASON
*Attesting Officer*

LUTRELLE F. PARKER
*Acting Commissioner of Patents and Trademarks*

UNITED STATES PATENT AND TRADEMARK OFFICE
CERTIFICATE OF CORRECTION

PATENT NO. : 4,013,718
DATED : March 22, 1977
INVENTOR(S) : Mario Guadalupi, Giorgio Pagani, Umberto Zardi and Ivo Paris It is certified that error appears in the above-identified patent and that said Letters Patent are hereby corrected as shown below:

First page, item "[75]", correct "Giorgia Pagani" to read

-- Giorgio Pagani --.

Signed and Sealed this

Twenty-fifth Day of April 1978

[SEAL]

Attest:

RUTH C. MASON
Attesting Officer

LUTRELLE F. PARKER
Acting Commissioner of Patents and Trademarks